United States Patent [19]

Smith et al.

[11] 4,022,794
[45] May 10, 1977

[54] NOVEL ANALOGS OF PROSTAGLANDINS WITH 4-OXO-THIAZOLIDINYL NUCLEUS AND METHOD OF PREPARATION THEREOF

[75] Inventors: Robert L. Smith, Lansdale; Ta-Jyh Lee, Hatfield; Edward J. Cragoe, Jr., Lansdale, all of Pa.

[73] Assignee: Merck & Co., Inc., Rahway, N.J.

[22] Filed: May 24, 1976

[21] Appl. No.: 689,318

[52] U.S. Cl. .......................... 260/295 R; 424/263; 424/270; 260/247.1 M; 260/268 H; 260/295 AM; 260/301; 260/306.7 R; 260/345.1; 260/345.7; 260/347.3; 260/347.7; 260/468 D; 260/483
[51] Int. Cl.$^2$ ............. C07D 401/02; C07D 277/02
[58] Field of Search ... 260/295 R, 296 R, 295 AM, 260/301, 306.7 R, 247.1 M

[56] References Cited
FOREIGN PATENTS OR APPLICATIONS
2,521,517  11/1975  Germany ...................... 260/302 R OTHER PUBLICATIONS
Ambrus et al, Prostaglandins, vol. 10, pp. 661–666 (Oct. 1975).

*Primary Examiner*—John D. Randolph
*Attorney, Agent, or Firm*—Thomas E. Arther; Harry E. Westlake, Jr.; Rudolph J. Anderson, Jr.

[57] ABSTRACT

This invention relates to novel 9-thia-, 9-oxothia-, and 9-dioxothia-11-oxo-12-azaprostanoic acid compounds, salts, and derivatives thereof and also to processes for the preparation of such compounds. These compounds have prostaglandin-like biological activity and are particularly useful as renal vasodilators, as platelet aggregation inhibitors, and for the treatment of certain autoimmune diseases.

39 Claims, No Drawings

NOVEL ANALOGS OF PROSTAGLANDINS WITH 4-OXO-THIAZOLIDINYL NUCLEUS AND METHOD OF PREPARATION THEREOF

SUMMARY OF THE INVENTION

This invention relates to novel 9-thia-, 9-oxothia-, and 9-dioxothia-11-oxo-12-azaprostanoic acid compounds, salts, and derivatives thereof. It also relates to compounds which are represented by the following structural formula:

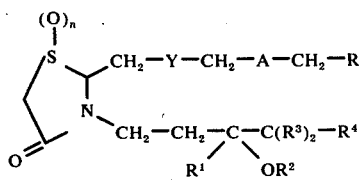

I wherein R is selected from the group consisting of carboxy and carboxy salt, said salt being formed from a pharmaceutically-acceptable cation, such as a metal cation derived from alkali metals, alkaline earth metals, and amines, such as ammonia, primary and secondary amines, and quaternary ammonium hydroxides. Especially-preferred metal cations are those derived from alkali metals, e.g., sodium, potassium, lithium, and the like, and alkaline earth metals, e.g., calcium, magnesium, and the like, and other metals, i.e., aluminum, iron, and zinc.

Pharmaceutically-acceptable cations derived from primary, secondary, or tertiary amines, or quaternary ammonium hydroxides are methylamine, dimethylamine, trimethylamine, ethylamine, N-methylhexylamine, benzylamine, α-phenethylamine, ethylenediamine, piperidine, morpholine, pyrrolidine, 1,4-dimethylpiperazine, ethanolamine, diethanolamine, triethanolamine, tris(hydroxymethyl)aminomethane, N-methylglucamine, N-methylglucosamine, ephedrine, procaine, tetramethylammonium hydroxide, tetraethylammonium hydroxide, benzyltrimethylammonium, and the like.

R is also selected from alkoxycarbonyl (—COOR$^5$) wherein R$^5$ is alkyl having 1–10 carbons atoms; carbamoyl (—CONH$_2$); substituted carbamoyl (—CONR$^6$R$^7$) wherein R$^6$ and R$^7$ are selected from the group consisting of hydrogen, lower alkyl having 1–4 carbon atoms, and diloweralkylaminoalkyl having 4–7 carbon atoms and carbazoyl (—CONHNH$_2$).

A is selected from the group consisting of methylene (—CH$_2$—) and oxygen (—O—).

Y is selected from the group consisting of ethylene (—CH$_2$—CH$_2$—), cis-vinylene

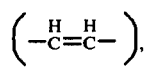

or ethynylene (—C ≡ C—).

n equals 0, 1, or 2.

R$^1$ is independently selected from the group consisting of hydrogen and methyl.

R$^2$ is selected from the group consisting of hydrogen and lower alkanoyl of 1–5 carbon atoms, e.g., formyl, acetyl, propionyl, butyryl, isobutryl, valeryl, pivaloyl, and the like.

R$^3$ is independently selected from the group consisting of hydrogen and methyl.

R$^4$ is selected from the group consisting of alkyl or branched alkyl of 3–6 carbon atoms (e.g., propyl, butyl, hexyl, isoamyl, 3,3-dimethylbutyl) or 4,4,4-trifluorobutyl.

Further:

In addition, when R$^4$ is straight chain alkyl and R$^1$ is methyl, the terminal carbon atoms of R$^4$ can be joined to R$^1$ (with abstraction of hydrogen) to form a carbocyclic ring of from 6–9 carbon atoms, or when R$^4$ is straight chain alkyl and R$^1$ is hydrogen, the terminal carbon atom of R$^4$ can be joined to the carbon bearing OR$^2$ to form a carbocyclic ring of from 5–8 carbon atoms.

Also, when R$^1$, R$^2$, and R$^3$ are hydrogen, R$^4$ can be a straight chain alkyl such that the terminal carbon atom of R$^4$ is joined to the hydroxy group oxygen atom (with abstraction of hydrogen) to form a cyclic ether containing 5- or 6-member atoms.

Further, R$^4$ can be OR$^{4a}$ where R$^{4a}$ is alkyl, branched alkyl of from 2–5 carbon atoms, substituted alkyl including 3,3,3-trifluoropropyl, 5- or 6-membered heterocyclic ring containing nitrogen or oxygen including pyridyl, furyl or furfuryl, or phenyl in which the phenyl ring can be substituted with one or two substituents selected from the group consisting of halogen, methyl, methoxy, or trifluoromethyl.

A preferred embodiment of this invention relates to 9-thia-, 9-oxothia-, and 9-dioxothia-11-oxo-12-azaprostanoic acids having the following general formula:

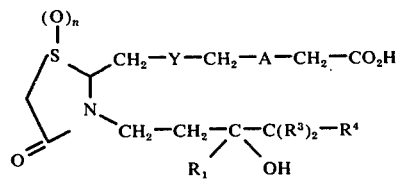

II wherein A is selected from the group consisting of methylene (—CH$_2$—) and oxygen (—O—); Y is selected from the group consisting of ethylene, cis-vinylene, or ethynylene; n is 0, 1, or 2; R$^1$ and R$^3$ are as defined above; and R$^4$ is alkyl, branched chain alkyl of 3–6 carbon atoms, 4,4,4-trifluorobutyl, or OR$^{4a}$ wherein R$^{4a}$ is as defined above.

It is to be noted that the carbon atom bearing the OR$^2$ group in formula I and the one bearing the hydroxyl group in formula II are asymmetric. This invention also covers stereoisomers in which the asymmetric center is exclusively in either one or the other of the two possible configurations, R and S.

BACKGROUND OF THE INVENTION

The compounds of formula I are described as 9-thia-, 9-oxothia-, and 9-dioxothia-prostanoids because of their structural relationship to the naturally-occurring prostaglandins.

The prostaglandins constitute a biologically prominent class of naturally-occurring, highly-functionalized C$_{20}$ fatty acids which are anabolized readily in a diverse array of mammalian tissues from three essential fatty acids; namely, 8,11,14-eicosatrienoic acid, 5,8,11, 14-eicosatetraenoic acid, and 5,8,11,14,17-eicosapentaenoic acid. Each known prostaglandin is a formal derivative of the parent compound, termed "prostanoic acid;" the latter is a C$_{20}$ fatty acid covalently bridged between carbons 8 and 12 such as to form a trans, vicinally-substituted cyclopentane in which the carboxy-bearing side chain is "alpha" or below the plane of the ring, and the other side chain is "beta" or above the plane of the ring as depicted in the formula below.

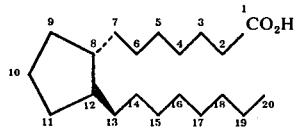

The six known primary prostaglandins, $PGE_1$, $PGE_2$, $PGE_3$, $PGF_{1\alpha}$, and $PGE_{2\alpha}$, and $PGF_{3\alpha}$, resulting directly from anabolism of the above-cited essential fatty acids via the action of prostaglandin synthetase, as well as the three prostaglandins resulting from in vivo dehydration of the PGE's, i.e., $PGA_1$, $PGA_2$, and $PGA_3$, are divided into three groups; namely,, the PGE, PGF, and PGA series on the basis of three distinct cyclopentane nuclear substitution patterns as illustrated below.

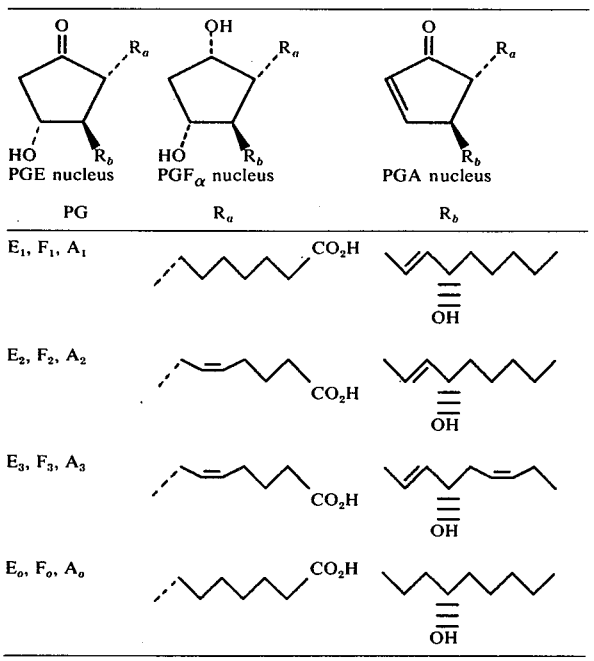

It should be noted that the arabic subscripts designate the number of carbon-carbon double bonds in the designated compound and that the Greek subscript used in the PGF series designates the stereochemistry of the C-9 hydroxyl group.

Further details connecting the prostaglandins can be found in the recent reviews of their chemistry [J. E. Pike, Fortschr. Chem. Org. Naturst., 28, 313 (1970) and G. F. Bundy, A. Rep. in Med. Chem., 7, 157 (1972)]; biochemistry [J. W. Hinman, A. Rev. Biochem., 41, 161 (1972)]; pharmacology [J. R. Weeks, A. Rev. Pharm., 12, 317 (1972)]; physiological significance [E. W. Horton, Physiol. Rev., 49, 122 (1969)]; and general clinical application [J. W. Hinman, Postgrad. Med. J., 46, 562 (1970)].

The naturally-occurring prostaglandins are known to have a broad spectrum of biological activity, but at the same time are unstable metabolically. More recently, analogs of the natural prostaglandins, such as 7-[3α(3-hydroxy-3-hydrocarbylpropyl)-4-hydroxy-tetrahydro-2β-thienyl(or 2β-furyl)]-heptanoic acid described in U.S. Pat. Nos. 3,881,017, issued Apr. 29, 1974, and 3,883,659, issued May 13, 1975, of Isidoros Vlattas, have been reported to have prostaglandin-like activity and also to have greater stability than the natural prostaglandins. Also, Belgian Pat. 828,994 discloses 4-(6-carboxyhexyl)-5-(3-hydroxy-1-trans-octenyl)thiazoles which are said to have activity analogous to prostaglandins and to inhibit prostaglandin-destroying enzymes.

The compounds of our invention represented by formula I hereinabove were synthesized with the goal of providing therapeutic agents with unique activity which is specific in its therapeutic action but with enhanced metabolic stability, thus providing a useful medicament which is active when administered orally as well as parenterally. This goal has been accomplished by the synthesis of the compounds of the present invention which are effective therapeutic agents for the treatment of certain human and animal diseases, including the control of blood clots, for the promotion of renal vasodilation, and as regulators of the immune response.

The compounds of the present invention are useful as pharmaceutically active compounds. Thus, these compounds are orally active in the treatment of conditions which are responsive to the actions of the natural prostaglandins. It is, of course, necessary to determine by routine laboratory testing which of the compounds of the present invention are most suitable for a specific end use and the recommended daily dosage.

In addition, the compounds of this invention appear to be broadly applicable in therapy as regulators of the immune response. The basis for their activity in this area is their ability to stimulate cyclic-AMP formation in cells. Agents, including the E type prostaglandins, that increase cellular cyclic-AMP concentration interfere with the cell-mediated immune response by inhibiting lymphocyte expression in response to antigen, by inhibiting release of pathological mediators from sensitized lymphocytes, and by inhibiting the killing of target cells by such lymphocytes. Various assays which depend upon the measurement of some function of the immunologically competent lymphocyte can be used to demonstrate that the prostaglandin analogs of this invention are similarly active. For example, the release of lymphokines (proteins that are agents of inflammation and tissue destruction) from sensitized lymphocytes in culture is strongly inhibited by these analgos in low concentrations. An example of the compounds of this invention which is particularly active in these assays is: 7-[3-(3-Hydroxyoctyl)-4-oxo-2-thiazolidinyl]heptanoic acid. Thus, it is apparent that the compounds of this invention are applicable to the treatment of those autoimmune diseases in whose pathogenesis a cell-mediated immune reaction is involved. Such diseases range from contact dermatitis to such chronic destructive diseases as rheumatoid arthritis and possibly multiple schlerosis and systemic lupus erythematosis.

The present prostaglandin analogs are also effective in preventing the rejection of transplanted organs. The biochemical basis for this action is the same as outlined in the preceding paragraph, for the rejection of organ grafts is considered to be predominantly a cell-mediated immune phenomenon and the hallmark of organ rejection is the infiltration of cytotoxic lymphocytes into the graft. Direct evidence that the compounds of this invention can retard or pervent transplant rejection has been obtained in the rat renal allograft model; in this system, administration of the present analog prevents the rejection of the transplanted kidney and the subsequent death of the host rat, which events invariably occur in the cases of untreated rats or those treated with the immunosuppressants.

In addition, certain of the compounds of this invention are particularly effective in inhibiting the aggregation in platelets in blood stimulated with collagen to cause platelet aggregation; and thus, in inhibiting platelet aggregation, they are useful in preventing thrombus formation. An example is: 7-[3-(3-Hydroxyoctyl)-4-oxo-2-thiazolidinyl]heptanoic acid.

Likewise, certain of the compounds of this invention are particularly effective in causing renal vasodilation in an in vivo assay in dogs. A particularly active compound in this assay is: 7-[3-(3-Hydroxyoctyl)-4-oxo-2-thiazolidinyl]heptanoic acid.

Because of their biological activity and ready accessibility, the compounds of the invention are also useful in that they permit large scale animal testing, useful and necessary to understanding of these various disease conditions such as rejection of organ grafts, stroke (thrombus formation), impaired renal circulation, and the like. It will be appreciated that not all of the compounds of this invention have these biological activities to the same degree, but the choice of any particular ones for any given purpose will depend upon several factors including the disease state to be treated.

The compounds of this invention can be administered either topically or systemically (i.e., intravenously, subcutaneously, intramuscularly, orally, rectally, or by aerosolization in the form of sterile implants for long action.

The pharmaceutical compositions can be sterile, injectable suspensions or solutions, or solid, orally-administrable, pharmaceutically-acceptable tablets or capsules; the compositions can also be intended for sublingual administration, or for suppository use.

Illustratively, a sterile, injectable composition can be in the form of aqueous or oleagenous suspensions or solutions.

The sterile, injectable composition can be an aqueous or oleagenous suspension or solution. Suspensions can be formulated according to the known art using suitable dispersing and wetting agents and suspending agents. Solutions are similarly prepared from the salt form of the compound.

Oily pharmaceutical carriers can also be used, since they dissolve the compound and permit high doses. Many oily carriers are commonly employed in pharmacetical use, such as, for example, mineral oil, lard, cottonseed oil, peanut oil, sesame oil, or the like.

It is preferred to prepare the compositions, whether aqueous or oils, in a concentration in the range of from 2–50 mg/ml. Lower concentrations require needless quantities of liquid. Higher concentrations than 50 mg./ml. are difficult to maintain and are preferably avoided.

Oral administration forms of the drug can also be prepared for laboratory animals or human patients provided that they are encapsulated for delivery in the gut. For either oral or parenteral use, the amount of drug to be administered is in the range of about 0.1 to 20 mg./kg. of body weight administered one to four times per day, the exact dose depending on the age, weight, and condition of the patient, and the fequency and route of administration.

The low cost and ready accessibility of the compounds of this invention make them particularly promising for applications in veterinary medicine in which field their utilities are comparable to those in human medicine.

PROCESS FOR THE SYNTHESIS OF COMPOUNDS OF THIS INVENTION

One of the preferred groups of compounds of the present invention is represented by the formula

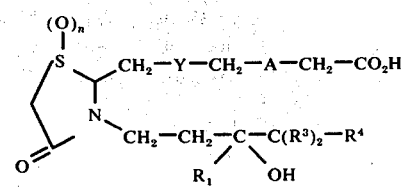

wherein A, Y, $n$, $R^1$, $R^3$, and $R^4$ are as previously stipulated. Compounds of this general type are synthesized by the following general synthetic method. This method essentially involves the condensation of an aldehyde of the formula

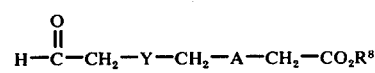

wherein A and Y are as previously defined and $R^8$ is straight chain lower alkyl (methyl or ethyl) with an amine of the formula

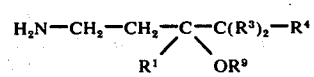

wherein $R^1$, $R^3$, and $R^4$ are as previously defined and $R^9$ is the tetrahydro-2H-pyran-2-yl group in the presence of a suitable drying agent such as sodium or magnesium sulfate to give key intermediate imine V of the formula

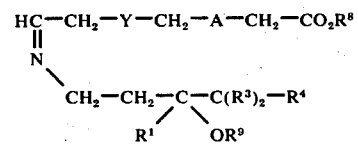

Subsequent condensation of imine V with mercaptoacetic acid provides a derivative of compound II in which the carboxy group is protected as an ester and the hydroxyl group as an ether. Hydrolysis of this derivative first with acid, then with base, provides one of the preferred sub-groups of compounds of this invention of formula II wherein $n=0$. This thia compound II is the converted by oxidation to the corresponding oxathia compound II of this invention wherein $n=1$ or the dioxothia compound II in which $n=2$. A detailed descrition of this method follows. (1) An aldehyde of the formula

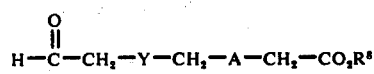

wherein A, Y, and $R^8$ are as previously defined is added slowly, preferably dropwise, to an amine of the formula

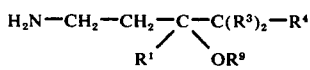

wherein $R^1$, $R^3$, $R^4$, and $R^9$ are as previously defined, maintained at a temperature of $-10°$ to $25°$ C. and, preferably, at $0°$ to $5°$ C. throughout the course of addition. Upon completing the aldehyde addition, the resulting reaction mixture is allowed to warm to room temperature, then is maintained at room temperature for 5 to 60 minutes, preferably for a period of 15 to 30 minutes, treated with a suitable inorganic drying agent, preferably sodium or magnesium sulfate, for a period of 5 60 minutes at room temperature under anhydrous conditions and filtered. The collected solid is washed with a low boiling aprotic solvent, preferably chloroform, ether, and the like, and the combined filtrate and washings are evaporated in vacuo at a temperature of $25°$ to $50°$ C. leaving the desired intermediate imine V as a residual oil.

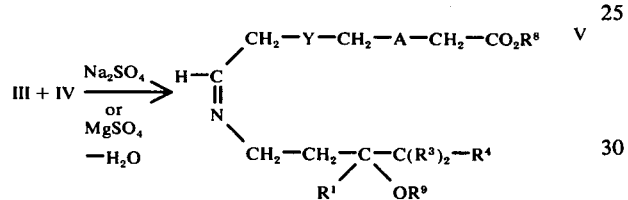

(2) Mercaptoacetic acid is added to a solution of imine V in an inert solvent, preferably a higher boiling solvent such as benzene, toluene, and the like, at room temperature. The resulting reaction solution is heated to and maintained at or near reflux in a Dean-Stark apparatus for a period of 2 to 24 hours to effect initial addition of the thiol compound across the imine linkage and subsequent ring closure of the intermediate amino acid with continuous removal of the liberated water providing an ester of formula VI

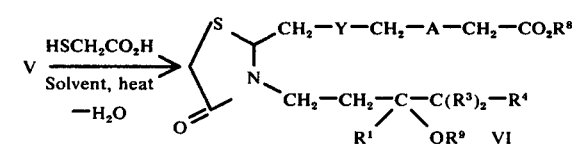

wherein A, Y, $R^1$, $R^3$, $R^4$, $R^8$, and $R^9$ are as previously defined. 3. Treatment of ester VI with a trace of a mineral acid such as concentrated hydrochloric acid in a protic solvent, preferably methanol, ethanol, and the like, at room temperature for a period of 1 to 24 hours, preferably overnight, provides an alcohol of formula VII

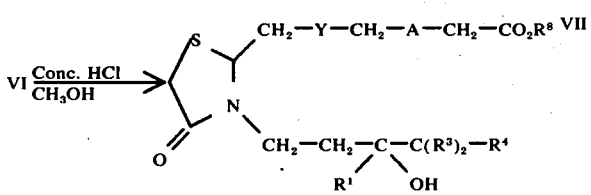

which is subsequently subjected to basic hydrolysis (dilute NaOH or KOH in methanol, ethanol, or tetrahydrofuran) at room temperature to remove the protecting ester function and, thereby, liberate an acid of formula VIII

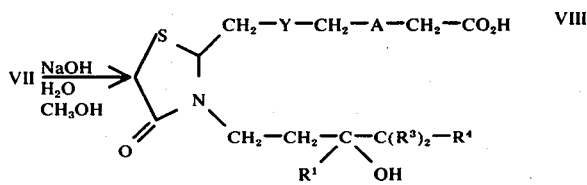

wherein A, Y, $R^1$, $R^3$, and $R^4$ are as previously defined. (4a) VIII is oxidized with sodium metaperiodate in an appropriate solvent such as aqueous ethanol at a temperature of $0°$ to $25°$ C., preferably $0°$ to $15°$ C., to provide sulfoxide products of this invention ($n=1$) of formula IX:

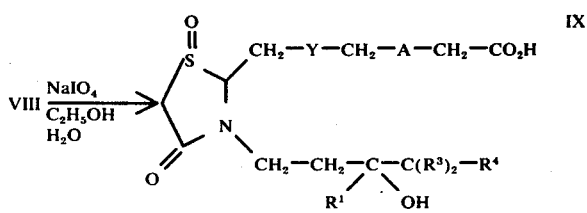

(4b) Either compounds VIII or IX can be oxidized with hydrogen peroxide (30% $H_2O_2$ in water) in a suitable solvent (ethanol, isopropanol, acetic acid, and the like) in the presence of a suitable catalyst such as ammonium molybdate. tetrahydrate at a temperature of from $0°$ to $30°$ C. for a period of from 24 to 72 hours to give the sulfones of this invention ($n=2$) of formula X:

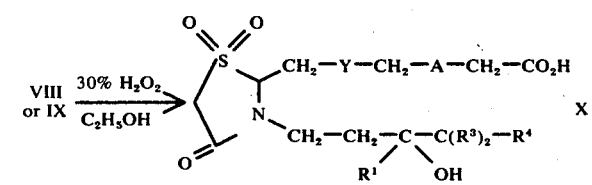

It should be noted that esters VII can be converted to the corresponding esters wherein $n=1$ or $n=2$ by oxidation as described in steps 4a and 4b, respectively. Subsequent hydrolysis (basic) of these esters provides acids IX and X, respectively.

Typical of the products which may be prepared by this method are:
7-[3-(3-hydroxyoctyl)-4-oxo-2-thiazolidinyl]heptanoic acid;
7-[3-(3-hydroxyoctyl)-1,4-dioxo-2-thiazolidinyl]heptanoic acid;
7-[3-(3-hydroxyoctyl)-1,1,4-trioxo-2-thiazolidinyl]-heptanoic acid;
7-{3-[4-(4-fluorophenoxy)-3-hydroxybutyl]-4-oxo-2-thiazolidinyl}heptanoic acid; and
7-{3-[2-(1-hydroxycyclohexyl)ethyl]-4-oxo-2-thiazolidinyl}heptanoic acid.

Frequently, it is advantageous from a therapeutic standpoint to prepare compounds of this invention (formula I) in which the asymmetric carbon atom bearing $R^1$ and $OR^2$ is exclusively in the R or S configuration. One should recall that the corresponding center in the natural prostaglandins is in the S configuration; inversion of this center frequently results in a reduction of biological activity, although sometimes a marked increase in biological specificity results from this configurational change.

In our series of 9-thia-, 9-oxothia-, and 9-dioxothia-11-oxo-12-azaprostanoids, compounds exclusively in the R and S configuration at this center can be produced by employing intermediate IV which is optically active, i.e., resolved into its respective R and S stereoisomeric forms.

We have found it particularly advantageous to employ an optically active reagant IVc,

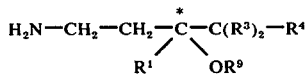

in which $R^1$, $R^3$, $R^4$, and $R^9$ are as previously defined and the carbon atom marked with an asterisk is exclusively in either the R or S configuration.

For example, the use of IVc in the general synthetic method gives intermediate imine Va

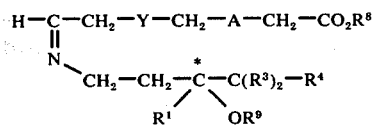

which is condensed with mercaptoacetic acid and subsequently deprotected by initial treatment with acid followed by basic hydrolysis to yield optically active product IIa of the invention wherein $n=0$ and the carbon marked with an asterisk is exclusively in either the R or S configuration. Subsequent oxidation of the latter product provides the corresponding optically active product IIa in which $n=1$ or 2.

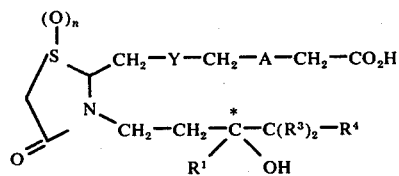

DERIVATIZATION OF PRODUCTS FROM THE MAJOR PROCESS

The directly obtained products of the general synthetic method described supra can be derivatized in a variety of ways to yield other products of formula I.

1. The fundamental process yields compounds in which R is carboxy. To obtain carboxy salts, the acid products are dissolved in a suitable solvent such as methanol, ethanol, tetrahydrofuran, and the like, and the resulting solution is treated with an appropriate alkalai or alkaline earth hydroxide or alkoxide to provide the metal salt, or with an equivalent quantity of ammonia, an amine, or a quaternary ammonium hydroxide to yield the amine salt. In each instance, the salt either separates from the solution directly and may be collected by filtration or, when the salt is soluble, it may be recovered by evaporation of the solvent or precipitated from solution by addition of a suitable nonpolar solvent such as ether, hexane, and the like. Aqueous solutions of the carboxylic acid salts can be prepared by treating an aqueous suspension of the carboxylic acid with an equivalent amount of an alkaline earth hydroxide or oxide, alkalai metal hydroxide, carbonate or bicarbonate, ammonia, an amine, or a quaternary ammonium hydroxide.

To obtain carboxy esters (i.e., compounds in which R is alkoxycarbonyl), the acid products are treated in ether with an ethereal solution of the appropriate diazoalkane. For example, methyl esters are produced by reaction of the acid products with diazomethane. To obtain products where R is carbamoyl, substituted carbamoyl, or carbazoyl, the acid product is initially converted to an active Woodward ester. For example, the acid product can be made to react with N-tert.-butyl-5-methylisoxazolium perchlorate in acetonitrile in the presence of a suitable base such as triethylamine to yield an active ester in which R is

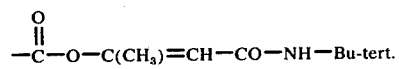

Active esters of this type can be reacted with ammonia to yield products of formula I where R is carbamoyl, with primary or secondary amines or di-lower-alkylaminoalkylamines to yield products in which R is substituted carbamoyl, i.e., $-CONR^6R^7$, and which hydrazine to yield products where R is carbazoyl.

2. The fundamental process yields products in which $R^2$ is hydrogen. In compounds wherein $R^1$ is hydrogen, reaction with formic acid, acetic anhydride, propionic anhydride, butyric anhydride, isobutyric anhydride, valeric anhydride, pivalic anhydride, and the like, without solvent and at temperatures from 25° to 60° C. provides compounds is which $R^2$ is formyl, acetyl, propionyl, butyryl, isobutyryl, valeryl, and pivaloyl, respectively.

3. Compounds of the invention in which Y is an unsaturated group such as vinylene or ethynylene can be hydrogenated in the presence of a suitable catalyst to other compounds of the invention wherein former ethynylene groups have been reduced to vinylene or ethylene, or former vinylene groups have been reduced to ethylene. Of particular interest is the hydrogenation of a Y ethynylene group over Lindlar catalyst to give a Y cis-vinylene group.

PREPARATION OF REAGENTS (1) The reagents III having the following general formula

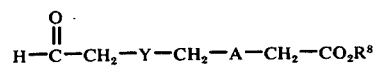

in which A, Y, and $R^8$ are as previously defined are prepared by the following process: An alcohol of formula $HO-CH_2-Y-CH_2-A-CH_2-CO_2R^8$ is oxidized using nickel peroxide (1.5 times theoretical quantity) in a suitable solvent, preferably ether, benzene, or petroleum ether, and the like, at a temperature of 10° to 50° C., preferably room temperature, for a period of 4 to 12 hours to provide an aldehyde

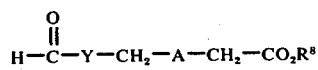

which is then made to react with methoxymethylenetriphenylphosphorane in a suitable solvent such as tetrahydrufuran, ether, and the like, at a temperature of 20° C. to the boiling point of the solvent for a period of 6 to 24 hours to yield the corresponding Wittig adduct CH₃OCH=CH—Y—CH₂—A—CH₂—CO₂R⁸. Treatment of the latter with perchloric acid-ether at room temperature for a period of 12 to 24 hours affords reagents III. When reagents III wherein Y is ethynylene are hydrogenated in the presence of Lindlar calatysts, reagents III in which Y is cis-vinylene are produced. In addition, hydrogenation of reagents III wherein Y is either ethynylene or cis-vinylene in the presence of a suitable catalyst such as 5% Pd/C provides reagents III in which Y is ethylene.

2. Reagents of the type IV

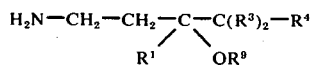   IV in which R¹, R³, R⁴, and R⁹ are as previously defined are prepared by the following process: Lithium diisopropylamide is made to react with acetonitrile in a suitable inert solvent such as tetrahydrofuran and the like, giving the anion Li⁺⁻CH₂—CN which is added to aldehydes (R¹ = hydrogen) or ketones (R¹ = methyl) of the formula R¹—CO—C(R³)₂—R⁴ to provide the alcohols NC—CH₂—C(OH)(R¹)—C(R³)₂—R⁴. Treatment of the latter with dihydropyran in the presence of a suitable acid catalyst such as p-toluenesulfonic acid at room temperature gives the corresponding O-THP derivatives (THP = the tetrahydro-2H-pyran-2-yl group) NC—CH₂—C(O—THP) (R¹)—C(R³)₂—R⁴ which are made to react with lithiumm aluminumhydride in a suitable inert solvent such as tetrahydrofuran, ether, and the like to afford the reagents IV.

3. The reagents IVa

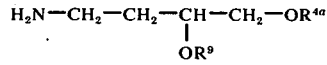   IVa are those of the type IV in which R¹ and R³ are hydrogen, R⁴ is OR⁴ᵃ, and R⁹ is as previously defined. Reagents IVa are prepared essentially by the same method as described for reagents IV in (2) starting with aldehydes H—CO—CH₂—OR⁴ᵃ. The latter are prepared by the following process: An alcohol or phenol R⁴ᵃ-OH is converted to the corresponding sodium alkoxide or phenoxide R⁴ᵃ-O⁻Na⁺ with sodium hydride in an aprotic solvent such as dimethylformamide which are then made to displace bromide from bromoacetaldehyde diethyl acetal to give the corresponding substituted diethyl acetals R⁴ᵃ—OCH₂—CH(OEt)₂. Acid hydrolysis of the latter in aqueous acetone provides the required aldehyde intermediates H-CO-CH₂-OR⁴ᵃ which are converted to the reagents IVa as described in process (2):

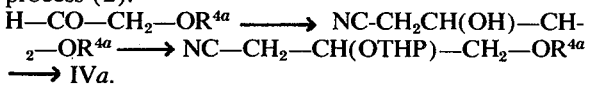

4. The reagents IVb

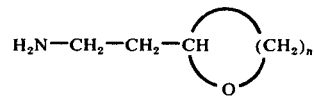   IVb are those of type IV in which R¹, R³, and R⁹ are hydrogen and R⁴ is a straight chain alkyl such that the terminal carbon atom of R⁴ is joined to the hydroxyl group oxygen atom (with abstraction of hydrogen) to form a cyclic ether with 5- or 6-member atoms (n=3 or 4). Treatment of acids

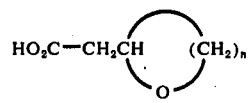

wherein n is as defined above with oxalyl chloride provides the corresponding acid chlorides

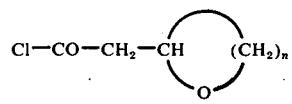

which are made to react with ammonia providing amides of the formula

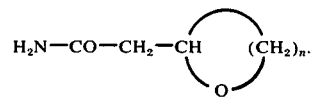

Reduction of the latter with lithiumaluminumhydride in a suitable inert solvent such as ether, tetrahydrofuran, and the like gives the reagents IVb.

5 The optically active reagents IVc

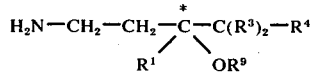   IVc are prepared by the following process:

Aldehydes (R¹ = hydrogen) or ketones (R¹ = methyl) of the formula R¹—CO—C(R³)₂—R⁴ are made to react with lithium acetylide or ethynylmagnesium bromide to give the alcohols H—C ≡ C—C(R¹)OH—C(R³)₂—R⁴. These alcohols are resolved into their optically active R and S enantiomers by standard methods of resolution (see Organic Reactions, Vol. II, Chapter 9, pages 376, John Wiley and Sons, Inc., N.Y., N.Y., 1944). After resolution, the individual enantiomers are separately and individually converted to their corresponding optically active reagents IVc as follows.

The resolved alcohols H-C ≡ C—C=(R¹)OH—C-(R³)₂—R⁴ are hydrogenated in a suitable solvent such as ethyl acetate in the presence of Lindlar catalyst to give the corresponding substituted allyl alcohols H₂C=CH—C=(R¹)OH—C(R³)₂—R⁴. These alcohols are converted to their alkoxides with sodium hydride in an inert polar solvent such as dimethylformamide and alkylated with benzyl bromide providing ethers of the formula H₂C=CH—C=(R¹)—(OCH₂C₆H₅)—C(R³)₂—R⁴. Hydroboration (reaction with diborane in tetrahydrofuran followed by H₂O₂ oxidation in the presence of aqueous sodium hydroxide) of the latter gives the corresponding primary alcohols HO—CH₂—CH₂—C=(R¹)—(OCH₂C₆H₅)—C(R³)₂—R⁴ which are oxidized with Collins reagent (chromium rioxide·pyridine complex in methylene chloride) providing aldehydes HCO—CH₂—C=(R¹) (OCH₂C₆H₅)—C(R³)₂—R⁴. Reductive amination of the latter using ammonium bromide (large excess) and sodium cyanoborohydride in a suitable solvent such as methanol, ethanol, and the like gives the corresponding primary amines H₂N—CH₂—C=(R¹)(OCH₂C₆H₅)—C(R³)₂—R⁴ which are hydrogenated in the presence of 5% Pd/C yielding alcohols H₂N—CH₂—CH₂—C=(R¹)OH—C(R³)₂—R⁴. Treatment of the latter with dihydropyran in the presence of p-toluenesulfonic acid (catalyst) gives optically active reagents IVc after neutralization with a suitable base such as aqueous potassium carbonate.

EXAMPLE 1

Preparation of 7-[3-(3-Hydroxyloctyl)-4-oxo-2-thiazolidinyl]-heptanoic Acid

Step A. Preparation of 1-Amino-3-(tetrahydro-2-H-pyran-2-yl-oxy)octane

Step A-1. Preparation of 3-Hydroxycaprylonitrile

A 1.9 M solution (21 ml., 40 millimole) of n-butyl lithium in hexane is added cautiously to a stirred solution of freshly distilled diisopropylamine (4.04 g., 40 millimole) in anhydrous tetrahydrofuran (60 ml.) maintained at 0° C. under a nitrogen atmosphere. The resulting solution is stirred at ambient temperature for 15 minutes, cooled to −78° C. and treated with a solution of anhydrous acetonitrile (1.64 g., 40 millimole) in anhydrous tetrahydrofuran (5 ml.). The resulting turbid suspension is stirred and maintained at −78° C. for 30 minutes and then treated with a solution of 1-hexanal (4.0 g., 40 millimole) in anhydrous tetrahydrofuran (5 ml.). After attaining a clear, yellow, reaction solution, cooling at −78° C. is maintained for an additional 15 minutes. The cold reaction solution is treated with 2N hydrochloric acid (50 ml.) and extracted with ether (100 ml.). The organic extract is washed with water (50 ml.) and 5% aqueous sodium bicarbonate (50 ml.), dried over magnesium sulfate, filtered, and evaporated in vacuo, leaving the title compound as a pale yellow oil (5.2 g., 92%) pmr (CDCl$_3$) δ 0.97 (3H, t), 2.55 (2H, d), 3.10 (H, s) and 3.93 (H, bs).

Step A-2. Preparation of 3-(Tetrahydro-2H-pyran-2-yloxy)caprylonitrile

A mixture of 3-hydroxycaprylonitrile (5.2 g., 36.8 millimole), dihydropyran (3.8 g., 45 millimole) and p-toluenesulfonic acid hydrate (catalytic amount) is stirred at 25° C. for 16 hours, then diluted with ether (100 ml.). The resulting solution is washed with 5% aqueous sodium hydroxide (25 ml.) and water (2 × 25 ml.), dried over magnesium sulfate and filtered. Evaporation of the filtrate in vacuo affords the title compound as a pale yellow oil (7.9 g., 95%), pmr (CDCl$_3$) δ 0.93 (3H, t), 2.54 (2H, q) and 4.68 (H, m).

Step A-3. Preparation of 1-Amino-3-(tetrahydro-2H-pyran-2-yloxy)octane

A solution of 3-(tetrahydro-2H-pyran-2-yloxy)-caprylonitrile (4.05 g., 18 millimole) in dry ether (10 ml.) is added dropwise to a stirred suspension of lithium aluminumhydride (0.76 g., 20 millimole) in dry ether (90 ml.) maintained under a nitrogen atmosphere. Upon completing the addition, the reaction mixture is stirred and heated at reflux for 16 hours. After cooling to 25° C., the reaction mixture is treated successively with water (1 ml.) and 5% aqueous sodium hydroxide (3 ml.) added dropwise with caution, affording a fine suspension which is cooled to and maintained at 0°–5° C. for 30 minutes and filtered. In vacuo evaporation of the solvent leaves the title compound as a pale yellow oil (3.95 g., 95%) pmr (CDCl$_3$) δ 0.88 (3H, t), 2.79 (2H, m) and 4.68 (H, bs).

Step B. Preparation of Methyl 7-[3-(3-Hydroxyoctyl)-4-oxo2-thiazolidinyl]heptanoate Methyl suberaldehydate (1.72 g., 10 millimole) is added dropwise to 1-amino-3-(tetrahydro-2H-pyran-2-yloxy)octane (2.41 g., 10.5 millimole) cooled at 0°–5° C. The resulting mixture is stirred and allowed to warm to 25° C., then maintained at 25° C. for 20 minutes. The reaction mixture is treated with anhydrous sodium sulfate (2 g.), stirred for 30 minutes at 25° C., and filtered. Collected solid is washed with chloroform (2 × 5 ml.). The combined filtrate and washings are evaporated in vacuo providing the desired intermediate imine as a pale yellow oil (ca. 4.4 g.), pmr (CDCl$_3$) δ 0.91 (t, 3H), 2.32 (t, 2H), 3.66 (s, 3H), 4.66 (bs, H) and 7.68 (vbs, H).

A solution of the oily imine (ca. 4.4 g.) in benzene (50 ml.) is cooled to 0°–5° C., treated with mercaptoacetic acid (0.92 g., 10 millimole) and then stirred and heated at reflux in a Dean-Stark apparatus for 16 hours. After cooling to 25° C., the reaction mixture is diluted with ether (100 ml.), washed with 5% aqueous sodium bicarbonate (25 ml.) and water (25 ml.), dried over magnesium sulfate, and filtered. Evaporation of the filtrate in vacuo leaves the tetrahydropyranyl ether of the title compound as a residual oil, pmr (CDCl$_3$) δ 0.93 (3H, t), 3.50 (2H, s), 3.66 (3H, s) and 4.66 (H, bs).

A solution of the oily tetrahydropyranyl ether in methanol (30 ml.) is treated with conc. hydrochloric acid (0.15 ml.) and stirred at 25° C. for 15 hours. After diluting with water (150 ml.), the reaction mixture is extracted with ether (150 ml.). The organic extract is washed with saturated aqueous brine (two times), dried over magnesium sulfate, filtered, and evaporated in vacuo providing a residual oil which is applied to a silica gel column (70 g.) with chloroform. Elution with chloroform-methanol (100:1; v:v; 305 ml.) provides impure material; continued elution with the same eluant (180 ml.) affords the title compound as a viscous oil (2.04 g., 55%), pmr (CDCl$_3$) δ 0.93 (t, 3H), 3.53 (s, 2H) and 3.62 (s, 3H).

Anal. Calcd. for $C_{19}H_{35}NO_4S$: C, 61.09; H, 9.44; N, 3.75 Found: C, 60.61; H, 9.60; N, 3.34.

Step C. Preparation of 7-[3-(3-Hydroxyoctyl)-4-oxo-2-thiozolidinyl] heptanoic Acid A solution of methyl 7-[3-(3-Hydroxyoctyl)-4-oxo-2-thiazolidinyl]heptanoate (0.87 g., 2.33 millimole) in methanol-water (5:2, v:v; 7 ml.) is treated with 5N sodium hydroxide (0.8 ml., 4.0 millimole) and stirred at 25° C. for 18 hours. The resulting reaction mixture is diluted with water (50 ml.), acidified to Congo Red with 2N hydrochloric acid and extracted with ether (100 ml.). The organic extract is washed with saturated aqueous brine (50 ml.), dried over magnesium sulfate, filtered, and evaporated in vacuo, leaving a residual oil which is applied to a silica gel column (20 g.) with chloroform. Elution with chloroformacetic acid (25:1; v:v; 70 ml.) provides a forerun which is discarded; continued elution with the same eluant (100 ml.) gives a slightly impure oil which is rechromatographed on silica gel (20 g.). After a forerun of chloroform-acetic acid (25:1; v:v; 70 ml.), continued elution with the same eluant (65 ml.) affords pure title compound as a viscous oil (0.43 g., 51%), pmr (CDCl$_3$) δ 0.93 (3H, t), 2.33 (2H, t), 3.58 (2H, s), 4.64 (H, m), and 8.02 (2H, s), D$_2$O-exchangeable).

Anal. Calcd. for C$_{18}$H$_{33}$NO$_4$S: C, 60.13; H, 9.25; N, 3.90 Found: C, 59.59; H, 9.40; N, 3.94.

EXAMPLE 2

Preparation of 7-[3-(3-Hydroxyoctyl)-1,4-dioxo-2-thiazolidinyl]heptanoic Acid

Sodium metaperiodate (0.75 g., 3.5 millimole) is added to a cold (0°–5° C.) solution of 7-[3-(3-hydroxyoctyl)-4-oxo-2-thiazolidinyl]heptanoic acid (1.24 g., 3.44 millimole) in methanol-water (5:4; v:v; 18 ml.). The resulting mixture is stirred and allowed to slowly warm to 25° C. (as the ice bath melts, etc.) over 16 hours. After removing the precipitated solid via filtration, the filtrate is diluted with cold water and extracted twice with chloroform. The organic extract is washed with saturated aqueous brine, dried over magnesium sulfate, filtered, and evaporated in vacuo leaving an oily residue which is chromatographed on silica gel (20 g.). Elution with chloroform-acetic acid (25:1; v:v) provides the title compound as a viscous, essentially colorless oil.

EXAMPLE 3

Preparation of 7-[3-(3-Hydroxyoctyl)-1,1,4-trioxo-2-thiazolidinyl]heptanoic Acid 30% Hydrogen peroxide (2.0 ml., 20 millimole) is added slowly to a stirred solution of 7-[3-(3-hydroxyoctyl)-1,4-dioxo-2-thiazolidinyl]heptanoic acid (1.98 g., 4.69 millimole) and ammonium molybdate:tetrahydrate (0.1 g., catalyst) in methanol (25 ml.) maintained at 0° to 5° C. The resulting solution is allowed to warm to room temperature and then is stirred at room temperature for 64 hours. After diluting with water, the reaction mixture is extracted with chloroform three times. The combined organic extract is washed with water until free of peroxides, dried over magnesium sulfate, and filtered. Evaporation of the filtrate in vacuo at 40° to 50° C. leaves a viscous oil which is applied to a silica gel (20 g.) column with chloroform. Elution with chloroform-acetic acid (25:1; v:v) provides the title compound as a tlc homogeneous oil.

EXAMPLE 4

Alternate Preparation of 7[3-(3-Hydroxyoctyl)-1,1,4-trioxo-2-thiazolidinyl]heptanoic Acid This compound is prepared and purified chromatographically essentially by the same procedure as described in Example 3 employing the following reagents:
7-[3-(3-Hydroxyoctyl)-4-oxo-2-thiazolidinyl]- heptanoic Acid — 1.27 g., 3.53 millimole
30% Hydrogen Peroxide — 1.5 ml., 15.0 millimole
Ammonium Molybdate . Tetrahydrate— 0.1 g., catalyst
Methanol-Water (4:1; v:v) — 20 ml.
Silica Gel — 20 g.
Chloroform-Acetic Acid (25:1; v:v) — 500 ml.

The title compound is obtained as a pale yellow, viscous oil identical in all respects to the product described in Example 3.

EXAMPLE 5

Preparation of 7-{3-[4-(4-Fluorophenoxy)-3-hydroxybutyl]-4oxo-2-thiazolidinyl}heptanoic Acid Step A-1. Preparation of 4-Fluorophenoxyacetaldehyde Diethyl Acetal A solution of 4-fluorophenol (28.1 g., 0.25 mole) in dry dimethylformamide (30 ml.) is added dropwise to a suspension of hexane (2 × 30 ml.) — prewashed sodium hydride (50% dispersion in mineral oil, 12.5 g., 0.26 mole) in dry dimethylformamide (120 ml.). After stirring at 25° C. for 10 minutes, the reaction mixture is treated with bromoacetaldehyde diethyl acetal (49.3 g., 0.25 mole) and heated at 100° C. for 4 hours. Upon cooling to 25° C., the reaction mixture is filtered to remove insoluble sodium bromide. The filtrate is evaporated in vacuo, leaving an oily residue which is triturated with acetone (100 ml.) at 25° C. and filtered to remove additional sodium bromide. Evaporation of the filtrate in vacuo provides a residual oil which is distilled to afford the title compound as a colorless oil (46.7 g., 82%), bp$_{0.05}$ 87° C.; pmr (CCl$_4$) δ 1.17 (6H, t), 3.57 (2H, q), 3.61 (2H, q), 3.85 (2H, d), 4.68 (H, t) and 6.6-7.1 (4H, m).

Step A-2. Preparation of 4-Fluorophenoxyacetaldehyde

A mixture of 4-fluorophenoxyacetaldehyde diethyl acetal (30 g., 0.13 mole), acetone (150 ml.), water (150 ml.) and concentrated sulfuric acid (0.8 ml.) is stirred and heated at reflux for 16 hours. After cooling to 25° C., the reaction mixture is extracted with methylene chloride four times. The combined organic extract is washed with aqueous sodium bicarbonate, dried over magnesium sulfate, and filtered. Evaporation of the filtrate in vacuo leaves a residual oil which is distilled to provide the title compound as a colorless oil (19 g., 94%) bp$_{0.05}$ 70° C.; pmr (CCl$_4$) δ 4.37 (2H, d), 6.6-7.1 (4H, m) and 9.68 (H, t).

Step A-3. Preparation of 4-(4-Fluorophenoxy)-3-hydroxybutyronitrile

This compound is prepared essentially by the same procedure as described in Example 1, Step a-1, employing the following reagents:
1.9M n-Butyl Lithium in Hexane — 21 ml., 40 millimole
Diisopropylamine, freshly-distilled — 4.04 g., 40 millimole
Tetrahydrofuran, Anhydrous — 70 ml.
Dry Autonitrile — 1.64 g., 40 millimole
4-Fluorophenoxyacetaldehyde — 6.17 g., 40 millimole
2N Hydrochloric Acid — 50 ml.
Ether — 100 ml.

The title compound is obtained as a pale yellow oil.

Step A-4. Preparation of 4-(4-Fluorophenoxy)-3-(tetrahydro-2H-pyran-2-yloxy)butyronitrile This compound is prepared essentially by the same procedure as described in Example 1, Step A-2, employing the following reagents:
4-(4-Fluorophenoxy)-3-hydroxybutyronitrile — 6.8 g., 35 millimole
Dihydropyran — 3.8 g., 45 millimole
p-Toluenesulfonic Acid.Hydrate — 0.1 g., catalyst Ether — 100 ml.

This procedure affords the title compound as a pale yellow oil.

Step A-5. Preparation of
1-Amino-4-(4-fluorophenoxy)-3-(tetrahydro-2H-pyran-2-yloxy)butane This compound is prepared essentially by the same procedure as described in Example 1, Step A-3, employing the following reagents:
4-(4-Fluorophenoxy)-3-(tetrahydro-2H-pyran2-yloxy)butyronitrile — 5.04 g., 18 millimole
Ether — 100 ml.
Lithium Aluminumhydride — 0.76 g., 20 millimole
Water — 1 ml.
5% Aqueous Sodium Hydroxide — 3 ml.

The title compound is obtained as a pale yellow oil.

Step B. Preparation of Methyl
7-{3-[4-(4-Fluorophenoxy)-3hydroxybutyl]-4-oxo-2-thiazolidinyl}heptanoate This compound is prepared essentially by the same procedure as described in Example 1, Step B, employing the following reagents;
Methyl Suberaldehydate — 1.72 g., 10 millimole
1-Amino-4-(4-fluorophenoxy)-3-(tetrahydro-2H-pyran-2-yloxy)butane — 2.89 g., 10.5 millimole
Anhydrous Sodium Sulfate — 2 g.
Chloroform — 10 ml.
Mercaptoacetic Acid — 0.92 g., 10 millimole
Benzene — 50 ml.
Ether — 100 ml.
Methanol — 30 ml.
Concentrated Hydrochloric Acid — 0.15 ml., catalyst
Silica Gel — 70 g.
Chloroform-Methanol (100:1; v:v) — 500 ml.

This procedure yields the title compound as a tlc homogeneous, viscous oil.

Step C. Preparation of
7-{3-[4-(4-Fluorophenoxy)-3-hydroxybutyl]-4-oxo-2-thiazolidinyl} heptanoic Acid This compound is prepared essentially by the same procedure as described in Example 1, Step C, employing the following reagents:
Methyl 7-{3-[4-(4-Fluorophenoxy)-3-hydroxybutyl]-4-oxo-2-thiazolidinyl}heptanoate — 1.02 g., 2.4 millimole
5N Sodium Hydroxide — 0.8 ml., 4.0 millimole
Methanol-Water (5:2; v:v) — 7 ml.
Silica Gel — 20 g.
Chloroform-Acetic Acid (25:1; v:v) — 250 ml.

The title compound is obtained as a pale yellow, viscous oil which is homogeneous via tlc analysis.

EXAMPLE 6

Preparation of
3-Oxa-7-[3-(3-Hydroxyoctyl)-4-oxo-2-thiazolidinyl]-5-heptynoic Acid Step A-1. Preparation of Methyl
3-Oxa-7-oxo-5-heptynoate Nickel peroxide (1.5 times the theoretical amount) is added to a solution of methyl 7-hydroxy-3-oxa-5heptynoate in dry ether. The resulting reaction mixture is magnetically stirred at room temperature for 6 hours providing a heterogeneous reaction mixture which is filtered to remove the insoluble inorganic solid. Collected solid is washed with ether. The combined filtrate plus washings is evaporated in vacuo at 40° to 50° C. leaving the title compound as a pale yellow oil which is used immediately in Step A-2.

Step A-2. Preparation of Methyl
8-Methoxy-3-oxa-5-octyn-7-enoate

A 1.9N solution of n-butyl lithium in hexane (5% excess) is added dropwise to a stirred suspension of methoxymethyltriphenylphosphonium chloride in anhydrous ether at room temperature maintained under a nitrogen atmosphere. After obtaining a deep red solution (ca. 15 minutes), the resulting ylide solution is treated with a solution of methyl 3-oxa-7-oxo-5-heptynoate (1 equivalent) in dry ether added dropwise at room temperature. The resulting reaction mixture is stirred at room temperature for 15 hours and then is heated to and maintained at reflux for ½ hour. After cooling to room temperature, the reaction mixture is diluted with ether and washed with water. The organic extract is dried over magnesium sulfate and filtered. Evaporation of the filtrate in vacuo at 40° C. leaves an oily residue which is chromatographed on silica gel to provide the title compound as a pale yellow oil.

Step A-3. Preparation of Methyl
3-Oxa-8-oxo-5-octynoate

A solution of methyl 8-methoxy-3-oxa-5-octyn-7-enoate in perchloric acid-ether is stirred at room temperature for 15 hours. The reaction mixture is diluted with ether and water and vigorously agitated for 5 minutes. After separating the phases, the organic extract is dried over sodium sulfate, filtered, and evaporated in vacuo at 40° to 50° C. leaving the title compound as an essentially colorless oil.

Step B. Preparation of Methyl
3-Oxa-7-[3-(3-hydroxyoctyl)-4-oxo-2-thiazolidinyl]-5-heptynoate This compound is prepared essentially by the same procedure as described in Example 1, Step B, except that the methyl suberaldehydate is replaced by methyl 3-oxa-8-oxo-5-octynoate. This procedure affords the title compound as a pale yellow, viscous oil after chromatographic purification on silica gel.

Step C. Preparation of
3-Oxa-7-[3-hydroxyoctyl)-4-oxo2-thiazolidinyl]-5-heptynoic Acid This compound is prepared essentially by the same method described in Example 1, Step C, except that the methyl 7-[3-(3-hydroxyoctyl)-4-oxo-2-thiazolidinyl]-heptanoate is replaced by methyl 3-oxa-7-[3-(3-hydroxyoctyl)-4-oxo-2-thiazolidinyl]-5-heptynoate. This method provides the title compound as a tlc homogeneous, viscous oil after chromatography on a silica gel column.

EXAMPLE 7

Preparation of
3-Oxo-7-[3-(3-hydroxyoctyl)-4-oxo-2-thiazolidinyl]-5-cis-heptenoic Acid A solution of 3-oxa-7-[3-(3-hydroxyoctyl)-4-oxo-2-thiazolidinyl]-5-heptynoic acid in ethyl acetate is magnetically stirred and hydrogenated at room temperature and atmospheric pressure in the presence of Lindlar catalyst until one molar equivalent of hydrogen has been consumed. After removing the catalyst by filtration, the filtrate is evaporated in vacuo at 40° to 50° C. leaving the title compound as an essentially colorless, viscous oil.

EXAMPLE 8

Preparation of
3-Oxa-7-[3-(3-hydroxyoctyl)-4-oxo-2-thiazolidinyl]-heptanoic Acid This compound is prepared essentially by the method as described in Example 7 except that the ethyl acetate and Lindlar catalyst are replaced by ethanol and 5% Pd/C (or 10% Pd/C), respectively. Hydrogenation of either 3-oxa-7[3-(3-hydroxyoctyl)-4-oxo-2-thiazolidinyl]-5-heptynoic acid or 3-oxa-7-[3-(3-hydroxyoctyl)-4-oxo-2-thiazolidinyl]-5-cis-heptenoic acid under these conditions provides the title compound as a viscous, essentially colorless oil. It should be noted that when the 5-heptynoic acid is employed, two moles of hydrogen per mole of substrate are consumed, whereas the corresponding 5-cis-heptenoic acid consumes one molar equivalent of hydrogen.

EXAMPLE 9

Preparation of
3-Oxa-7-[3-(3-hydroxyoctyl)-1,4-dioxo-2-thiazolidinyl]-5-cis-heptenoic Acid This compound is prepared essentially by the method as described in Example 2 except that the 7-[3-(3-hydroxyoctyl)-4-oxo-2-thiazolidinyl]heptanoic acid is replaced by 3-oxa-7-[3-(3-hydroxyoctyl)-4-oxo-2-thiazolidinyl]-5-cis-heptenoic acid. This method gives the title compound as a viscous, pale yellow oil.

EXAMPLE 10

Preparation of
3-Oxa-7-[3-(3-hydroxyoctyl)-1,1,4-trioxo-2-thiazolidinyl]-5-cis-heptenoic Acid This compound is prepared essentially by the method as described in Example 3 except that the 7-[3-(3-hydroxyoctyl)-1,4dioxo-2-thiazolidinyl]heptanoic acid is replaced by 3-oxa-7-[3-(3-hydroxyoctyl)-1,4-dioxo-2-thiazolidinyl]-5-cis-heptenoic acid. The title compound is obtained as a pale yellow, viscous oily product using this method.

EXAMPLE 11

Preparation of
3-Oxa-7-[3-(3-hydroxyoctyl)-1,4-dioxo-2-thiazolidinyl]heptanoic Acid This compound is prepared essentially by the method as described in Example 8 except that the 3-oxa-7-[3-hydroxyoctyl)-4-oxo-2-thiazolidinyl]-5-heptynoic acid is replaced by 3-oxa-7-[3-(3-hydroxyoctyl)-1,4-dioxo-2-thiazolidinyl]-5-cis-heptenoic acid. This method yields the title compound as a viscous, pale yellow oil.

Example 12

Preparation of
3-Oxa-7-[3-(3-hydroxyoctyl)-1,1,4-trioxo-2-thiazolidinyl]heptanoic Acid This compound is prepared essentially by the same method as described in Example 8 except that the 3-oxa-7-[3-(3-hydroxyoctyl)-4-oxo-2-thiazolidinyl]-5-heptynoic acid is replaced by 3-oxa-7-[3-(3-hydroxyoctyl)-1,1,4-trioxo-2-thiazolidinyl]-5-cis-heptenoic acid. This process yields the title compound as a viscous, pale yellow oil.

Example 13

Preparation of
7-{3-[2-(tetrahydro-2H-pyran-2yl)ethyl]-4oxo-2-thiazolidinyl}heptanoic Acid

Step A. Preparation of Methyl 7-{3-[2-(Tetrahydro-2H-pyran-2-yl)ethyl]-4-oxo-2-thiazolidinyl}heptanoate This compound is prepared essentially by the same method as described in Example 1, Step B, except that the 1-amino-3-(tetrahydro-2H-pyran-2-yloxy)octane is replaced by 1-amino-2-(tetrahydro-2H-pyran-2yl)ethane and the treatment with methanol-acid is not needed. This method affords the title compound as an essentially colorless, viscous oil.

Step B. Preparation of 7-{3-[2-(Tetrahydro-2H-pyran-2-yl)-ethyl]-4-oxo-2-thiazolidinyl}heptanoic Acid This compound is prepared essentially by the same method as described in Example 1, Step C, except that the methyl 7-[3-(3-hydroxyoctyl)-4-oxo-2-thiazolidinyl]heptanoate is replaced by methyl 7-{3-[2-(tetrahydro-2H-pyran-2-yl)-ethyl]-4-oxo-2-thiazolidinyl}heptanoate. After careful chromatographic purification on silica gel, the title compound is obtained as a viscous, pale yellow oil.

EXAMPLE 14

Preparation of
7-{3-[2-(1-Hydroxycyclohexyl)ethyl]-4-oxo-2thiazolidinyl}heptanoic Acid

Step A-1. Preparation of 2-(1-Hydroxycyclohexyl)acetonitrile

This compound is prepared essentially by the same procedure as described in Example 1, Step A-1, employing the following reagents:
Diisopropylamine, freshly-distilled — 20.2 g., 0.2 mole
1.6N n-Butyllithium in Hexane — 125 ml., 0.2 mole
Tetrahydrofuran — 290 ml.
Cyclohexanone — 19.6 g., 0.2 mole
Hexamethylphosphoric Triamide — 15 ml.
Ether — 100 ml.

The title compound is obtained as a pale yellow oil (23.6 g., 85%), pmr (CDCl$_3$) δ 1.64 (8H, bs), 2.54 (2H, s) and 2.64 (H, s, D$_2$O-exchangeable).

Step A-2. Preparation of 2-[1-(Tetrahydro-2H-pyran-2-yloxy)-cyclohexyl]acetonitrile This compound is prepared essentially by the same method as described in Example 1, Step A-2, except that the 3-hydroxycaprylonitrile is replaced by 2-(1-hydroxycyclohexyl)acetonitrile. This method provides the title compound as a pale yellow liquid.

Step A-3. Preparation of 1-Amino-2-[1-(tetrahydro-2H-pyran-2-yloxy)cyclohexyl]ethane This compound is prepared essentially by the same method as described in Example 1, Step A-3, except that the 3-(tetrahydro-2H-pyran-2-yloxy)caprylonitrile is replaced by a 2-[1-(tetrahydro-2H-pyran-2-yloxy)cyclohexyl]acetonitrile. This process yields the title compound as a pale yellow oil.

Step B. Preparation of Methyl 7-{3-[2-(1-Hydroxycyclohexyl)-ethyl]-4-oxo-2-thiazolidinyl}heptanoate This compound is prepared essentially by the same method as described in Example 1, Step B, except that the 1-amino-3-(tetrahydro-2H-pyran-2-yloxy)octane is replaced by 1-amino-2-[1-(tetrahydro-2H-pyran-2-yloxy)cyclohexyl]ethane. This method provides the title compound as an essentially colorless, viscous oil.

Step C. Preparation of 7-{3-[2-(1-Hydroxycyclohexyl)ethyl]-4-oxo-2-thiazolidinyl}heptanoic Acid This compound is prepared essentially by the same method as described in Example 1, Step C, except that the methyl 7-[3-(3-hydroxyoctyl)-4-oxo-2-thiazolidinyl]heptanoate is replaced by methyl 7-{3-[2-(1-hydroxycyclohexyl)ethyl]-4-oxo-2-thiazolidinyl} heptanoate. Chromatographic purification of the crude product resulting from this method gives the title compound as a tlc homogeneous, viscous oil.

EXAMPLE 15

Preparation of 7-[3-(3-(S)-Hydroxyoctyl)-4-oxo-2-thiazolidinyl]heptanoic Acid

Step A-1. Preparation of 3(S)-Hydroxy-1-octene

This compound is prepared essentially by the same method as described in Example 7 except that the 3-oxa-7-[3(3-hydroxyoctyl)-4-oxo-2-thiazolidinyl]-5-heptynoic acid is replaced by (S)-1-octyn-3-ol. This method gives the title compound as an essentially colorless liquid.

Step A-2. Preparation of 3(S)-benzyloxy-1-octene

A solution of 3(S)-hydroxy-1-octene (6.41 g., 0.05 mole) in dry dimethylformamide is added dropwise to a stirred suspension of hexane (2 × 10 ml. ) — prewashed sodium hydride (50% dispersion in mineral oil, 2.64 g., 0.055 mole) in dry dimethylformamide (45 ml.) at 25° C. Upon cessation of gas evolution, the reaction mixture is cooled to 0° to 5° C. and treated with a solution of benzyl bromide (10.3 g., 0.06 mole) in dry dimethylformamide (10 ml.). The resulting mixture is stirred at 25° C. for 16 hours, then is heated at 100° C. for 1 hour. After cooling to 25° C., the reaction mixture is diluted with ice water (50 ml.) and extracted with ether four times. The combined organic extract is washed with 2N hydrochloric acid and saturated aqueous brine, dried over magnesium sulfate and filtered. In vacuo evaporation of the filtrate leaves an oily residue which affords the title compound upon distillation as a colorless oil.

Step A-3. Preparation of 3(S)-Benzyloxy-1-octanol

A solution of borontrifluoride:etherate (2.1ml.; 16.7 millimole) in dry tetrahydrofuran (5 ml.) is added dropwise to a stirred mixture of 3(S)-benzyloxy-1-octene (2.19 g., 10 millimole) and sodium borohydride (0.47 g., 12.5 millimole) in dry tetrahydrofuran (25 ml.) maintained at 0° to 5° C. under a nitrogen atmosphere. The resulting reaction mixture is warmed to and maintained at room temperature for 15 hours. After cooling to 0° to 5° C., the reaction mixture is treated cautiously via successive dropwise additions with water (2 ml.), 5N sodium hydroxide (4 ml.) and 30% hydrogen peroxide (8 ml.). After stirring at room temperature for ½ hour, the resulting mixture is diluted with ice water and extracted with chloroform three times. The combined organic extract is washed with saturated aqueous brine, dried over magnesium sulfate, and filtered. Evaporation of the filtrate in vacuo provides the title compound as a viscous oil (2.37 g., 100%).

Step A-4. Preparation of 3(S)-Benzyloxy-1-octanal

Chromium trioxide (6.0 g., 0.06 mole) is added to a mechanically-stirred solution of dry pyridine (9.49 g., 0.12 mole) in methylene chloride (150 ml.) maintained at 0°-5° C. under a nitrogen atmosphere. The resulting reaction mixture is warmed to 25° C., stirred at 25° C. for ⅓ hour, and treated with a solution of 3(S)-benzyloxy-1-octanol (2.37 g., 0.01 mole) in methylene chloride (2 ml.) which initiates precipitation of a black, intractable precipitate. After stirring at 25° C. for ¼ hour, the solution is decanted, and the insoluble precipitate washed with ether (200 ml.). The combined decantates are washed successively with 5% sodium hydroxide (3 × 100 ml.), 5% hydrochloric acid (100 ml.), and 5% aqueous sodium bicarbonate (100 ml.); dried over magnesium sulfate; and filtered. In vacuo evaporation of the filtrate affords the title compound as a pale yellow oil.

Step A-5. Preparation of 1-Amino-3(S)-benzyloxyoctane

Sodium cyanoborohydride (5% excess over theoretical amount) is allowed portionwise over ½ hour to a stirred mixture of 3-(S)-benzyloxy-1-octanal (1 molar equivalent) and ammonium bromide (15 molar equivalents) in methanol at room temperature. The resulting reaction mixture is stirred at room temperature for 48 hours, then is cooled to 0° to 5° C. and cautiously treated with concentrated hydrochloric acid to destroy excess hydride reagent. The resulting reaction mixture is evaporated in vacuo at or below 40° C. leaving a residual mass which is partitioned between 5% hydrochloric acid and ether. The aqueous phase is separated, slowly basicified with potassium carbonate, and extracted with ether three times. The combined organic extract is washed with saturated aqueous brine, dried over sodium sulfate, and filtered. In vacuo evaporation of the filtrate leaves the title compound as an essentially colorless oil.

Step A-6. Preparation of 1-Amino-3-(S)-octanol

This compound is prepared essentially by the same method as described in Example 8 except that the 3-oxa-7-[3-(3-hydroxyoctyl)-4-oxo-2-thiazolidinyl]-5-heptynoic acid is replaced by 1-amino-3(S)-benzyloxyoctane. This method provides the title compound as a pale yellow oil.

Step A-7. Preparation 1-Amino-3(S)-(tetrahydro-2H-pyran-2-yloxy)octane

This compound is prepared essentially by the same method as described in Example 1, Step A-2, except that the 3-hydroxycaprylonitrile is replaced by 1-amino-3(S)-octanol and slightly more than one equivalent of p-toluenesulfonic acid-hydrate is used. This method provides the p-toluenesulfonic acid salt of the title compound which is converted to the oily title compound by distribution between dilute sodium hydroxide and ether. The organic phase is washed with saturated aqueous brine, dried over sodium sulfate, and filtered. Evaporation of the filtrate in vacuo leaves the title compound as a residual oil.

Step B. Preparation of Methyl 7-[3-(3(S)-Hydroxyoctyl)-4-oxo-2-thiazolidinyl]heptanoate This compound is prepared essentially by the same method as described in Example 1, Step B, except that the 1-amino-3-(tetrahydro-2H-pyran-2-yloxy)octane is replaced by the 3(S)-enantiomer. The title compound is obtained as a viscous oil identical via tlc behavior to that obtained in Example 1, Step B.

Step C. Preparation of 7-[3-(3(S)-Hydroxyoctyl)-4-oxo-2thiazolidinyl]heptanoic Acid This compound is prepared essentially by the same method as described in Example 1, Step C, except that the methyl 7-[3-(3-hydroxyoctyl)-4-oxo-2-thiazolidinyl]heptanoate is replaced by the 3(S)-enantiomer. After chromatographic purification on silica gel, this process gives the title compound as a viscous oil which displays tlc properties identical to those displayed by the racemate obtained in Example 1, Step C.

EXAMPLE 16

Preparation of 7-[3(3(R)-Hydroxyoctyl)-4-oxo-2-thiazolidinyl]heptanoic Acid

By following exactly the same methods described in Example 15 but beginning with (R)-1-octyn-3-ol instead of (S)-1-octyn-3-ol, there are obtained successively:
Step A-1, 3(R)-Hydroxy-1-octene;
Step A-2, 3(R)-Benzyloxy-1-octene;
Step A-3, 3(R)-benzyloxy-1-octanol;
Step A-4, 3(R)-Benzyloxy-1-octanal;
Step A-5, 1-Amino-3-(R)-benzyloxyoctane;
Step A-6, 1-Amino-3(R)-octanol;
Step A-7, 1-Amino-3 -(R)-(tetrahydro-2H-pyran-2-yloxy)octane;
Step B, Methyl 7-[3-(3(R)-Hydroxyoctyl)-4-oxo-2-thiazolidinyl]heptanoate; and
Step C, 7-[3-(3(R)-Hydroxyoctyl)-4-oxo-2-thiazolidinyl]heptanoic acid.

EXAMPLE 17

Preparation of 7-[3-(3-Hydroxy-3-methyloctyl)-4-oxo-2-thiazolidinyl]heptanoic Acid By following exactly the same procedures described in Example 1 but beginning with 2-heptanone instead of 1-hexanal, there are obtained successively:
Step A-1, 3-Hydroxy-3-methylcaprylonitrile;
Step A-2, 3-Methyl-3-(tetrahydro-2H-pyran-2-yloxy)-caprylonitrile;
Step A-3, 1-Amino-3-methyl-3-(tetrahydro-2H-pyran-2-yloxy)octane;
Step B, Methyl 7-[3-(3-hydroxy-3-methyloctyl)-4-oxo-2thiazolidinyl]heptanoate; and
Step C, 7-[3-(3-hydroxy-3-methyloctyl)-4-oxo-2-thiazolidinyl]heptanoic acid.

EXAMPLE 18

Preparation of 7-[3-(3-Hydroxy-4,4-dimethyloctyl)-4-oxo-2thiazolidinyl]heptanoic Acid By following exactly the same procedures described in Example 1 but beginning with 2,2-dimethyl-1-hexanal rather than 1-hexanal, there are obtained successively:
Step A-1, 3-Hydroxy-4,4-dimethylcaprylonitrile;
Step A-2, 3-(Tetrahydro-2H-pyran-2-yloxy)-4,4-dimethylcaprylonitrile;
Step A-3, 1-Amino-3-(tetrahydro-2H-pyran-2-yloxy)-4,4-dimethylcaprylonitrile;
Step B, Methyl 7-[3-(3-hydroxy-4,4-dimethyloctyl)-4-oxo2-thiazolidinyl]heptanoate; and
Step C, 7-[3-(3-Hydroxy-4,4-dimethyloctyl)-4-oxo-2-thiazolidinyl]heptanoic acid.

EXAMPLE 19

Preparation of 7-[3-(3-Hydroxy-8,8,8-trifluorooctyl)-4-oxo2-thiazolidinyl]heptanoic Acid By following exactly the same procedures described in Example 1 but beginning with 6,6,6-trifluorohexanal instead of 1-hexanal, there are obtained successively:
Step A-1, 3-Hydroxy-8,8,8-trifluorocaprylontrile;
Step A-2, 8,8,8-Trifluoro-3-(tetrahydro-2H-pyran-2-yloxy)caprylonitrile;
Step A-3, 1-Amino-8,8,8-trifluoro-3-(tetrahydro-2H-pyran-2-yloxy)octane;
Step B, Methyl 7-[3-(3-Hydroxy-8,8,8-trifluorooctyl)-4-oxo-2-thiazolidinyl]heptanoate; and
Step C, 7-[3-(3-Hydroxy-8,8,8-trifluorooctyl)4-2-thiazolidinyl]heptanoic acid.

EXAMPLE 20

Preparation of 7-{3-[3-Hydroxy-4-(3-pyridyloxy)butyl]-4-oxo2-thiazolidinyl}heptanoic Acid By following exactly the same procedures described in Example 5 but beginning with 3-hydroxypyridine rather than 4-fluorophenol, there are obtained in order:
Step A-1, 3-Pyridyloxyactaldehyde diethyl acetal;
Step A-2, 3-Pyridyloxyacetaldehyde;
Step A-3, 3-Hydroxy-4-(3-pyridyloxy)butyronitrile;
Step A-4, 4-(3-Pyridyloxy)-3-(tetrahydro-2H-pyran-2-yloxy)butyronitrile;
Step A-5, 1-Amino-4-(3-pyridyloxy)-3-(tetrahydro-2H-pyran-2yloxy)butane;
Step B, Methyl {7- 3-[3-Hydroxy-4-(3-pyridyloxy)-butyl]-4oxo-2-thiazolidinyl}heptanoate; and
Step C, 7-{3-[3-Hydroxy-4-(3-pyridyloxy)butyl]-4-oxo-2thiazolidinyl}heptanoic acid.

EXAMPLE 21

Preparation of 7-[3-(3-Hydroxy-4-propoxybutyl)-4-oxo-2-thiazolidinyl]heptanoic Acid The synthesis of this compound is carried out by the procedures of Example 5 except 1-propanol is used in Step A-1 instead of 4-fluorophenol. Thus, there are obtained in succession:
Step A-1, Propoxyacetaldehyde diethyl acetal;
Step A-2, Propoxyacetaldehyde;
Step A-3, 3-Hydroxy-4-propoxybutyronitrile;

Step A-4, 4-Propoxy-3-(tetrahydro-2H-pyran-2-yloxy)-butyronitrile;
Step A-5, 1-Amino-4-propoxy-3-(tetrahydro-2H-pyran-2-yloxy)butane;
Step B, Methyl 7-[3-(3-Hydroxy-4-propoxybutyl)-4-oxo-2thiazolidinyl]heptanoate; and
Step C, 7-[3-(3-Hydroxy-4-propoxybutyl)-4-oxo-2-thiazolidinyl]heptanoic acid.

EXAMPLE 22

Preparation of 7-[3-(3-Hydroxy-4-propoxybutyl)-1,4-dioxo-2-thiazolidinyl]heptanoic Acid This compound is prepared essentially by the same method as described in Example 2 except that the 7-3-(3-hydroxyoctyl)-4-oxo-2-thiazolidinyl]heptanoic acid is replaced by 7-[3-(3-hydroxy-4-propoxybutyl)-4-oxo-2-thiazolidinyl]heptanoic acid. This method provides the title compound as an essentially colorless, viscous oil.

EXAMPLE 23

Preparation of 7-[3-(3-Hydroxy-4-propoxybutyl)-1,1,4-thioxo-2-thiazolidinyl]heptanoic Acid This compound is prepared essentially by the same procedure as described in Example 3 except that the 7-[3-(3-hydroxyoctyl)-1,4-dioxo-2-thiazolidinyl]heptanoic acid is replaced by 7-[3-(3-hydroxy-4-propoxybutyl)-1,4-dioxo-2-thiazolidinyl]heptanoic acid. Chromatographic purification of the resulting product on silica gel gives the title compound as a viscous, pale yellow oil.

EXAMPLE 24

Preparation of Ethyl 7-[3-(3-Hydroxy-4-propoxybutyl)-1,4-dioxo-2-thiazolidinyl]heptanoate A solution of diazoethane (approximately 3.4 g., 0.06 mole) in ether (100 ml.) is slowly added to a solution of 7-[3-(3-hydroxy-4-propoxybutyl)-1,4-dioxo-2-thiazolidinyl]heptanoic acid (11.3 g., 0.03 mole) in ether (50 ml.) with stirring and cooling (0° to 5° C.). The resulting solution is allowed to warm to and stand at room temperature for 4 hours. After destroying excess diazoethane with acetic acid, the reaction solution is washed with 5% sodium bicarbonate solution and water, dried over sodium sulfate, and filtered. In vacuo evaporation of the filtrate leaves the title compound as an essentially colorless, viscous oil.

EXAMPLE 25

Preparation of 7-[3-(3-Acetyloxyoctyl)-4-oxo-2-thiazolidinyl]heptanoic Acid

A mixture of 7-[3-(3-hydroxyoctyl)-4-oxo-2-thiazolidinyl]heptanoic acid (9.0 g., 0.025 mole) and acetic anhydride (0.1 g., 0.06 mole) is heated at 60° C. for 18 hours. The resulting mixture is cooled to room temperature and dissolved in ethyl acetate providing a clear solution which is extracted with an ice-cold solution of sodium hydroxide (8 g.) in water (150 ml.). The basic solution is quickly separated and acidified with concentrated hydrochloric acid. The oily acid which separates is extracted with ether. The organic extract is washed with water, dried over sodium sulfate, and filtered. Evaporation of the filtrate in vacuo at 40° to 50° C. leaves a residual oil which is purified via application to a silica gel (150 g.) column with chloroform. Elution with chloroform-methanol (99.1; v:v) provides the title compound as a colorless, viscous oil.

By replacing the acetic anhydride used in Example 25 with an equivalent quantity of propionic anhydride, butyric anhydride, isobutyric anhydride, valeric anhydride, or pivalic anhydride and conducting the reaction as described in Example 25, there is obtained:
7-[3-(3-Propionyloxyoctyl)-4-oxo-2-thiazolidinyl]heptanoic acid,
7-[3-(3-Butyryloxyoctyl)-4-oxo-2-thiazolidinyl]heptanoic acid,
7-[3-(3-Isobutyryloxyoctyl)-4-oxo-2-thiazolidinyl]heptanoic acid,
7-[3-(3-Valeryloxyoctyl)-4-oxo-2-thiazolidinyl]heptanoic acid, and
7-[3-(3-Pivaloyloxyoctyl)-4-oxo-2-thiazolidinyl]heptanoic acid, respectively.

EXAMPLE 26

Preparation of N-(2-Dimethylaminoethyl)-7-[3-(3-hydroxyoctyl)-4-oxo-2-thiazolidinyl]heptanamide A solution of 7-[3-(3-hydroxyoctyl)-4-oxo-2-thiazolidinyl]heptanoic acid (3.6 g., 10 millimole), Example 1, triethylamine (1.74 ml., 12.5 millimole) and distilled water (18 ml., 1.0 mole) in acetonitrile (100 ml.) is treated with N-t-butyl-5-methylisoxazolium perchlorate (3.0 g., 12.5 millmole). The resulting solution is evaporated in vacuo (water aspirator) at 20° to 23° C. for 4 hours providing a tacky residue which is triturated with water (150 ml.) at 0° to 5° C. for 15 minutes. After decanting the aqueous phase, the oily residue is dissolved in benzene-ether (1:1, v:v, 200 ml.). The organic extract is dried over sodium sulfate, filtered, and evaporated in vacuo at 35° to 40° C. providing the desired "active ester", N-t-butyl-3-{[3-(3hydroxyoctyl)-4-oxo-2-thiazolidinyl]heptanoyloxy-} crotonamide, as a pale yellow oil.

A solution of 2-dimethylaminoethylamine (0.88 g., 10 millimole) in acetonitrile (25 ml.) is added to a solution of the "active ester" in acetonitrile (25 ml.) providing a clear solution which is stirred at 25° C. for 17 hours. The solvent is removed in vacuo at 40° to 50° C. leaving a residual oil which is partitioned between ether (200 ml.) and water (2 × 100 ml.). The organic extract is washed with saturated aqueous brine (2 × 100 ml.), dried over sodium sulfate, filtered, and evaporated in vacuo at 40° to 50° C. providing a crude, tan oil.

The oil is partitioned between 5% hydrochloric acid (100 ml.) and ether (2 × 100 ml.). The aqueous acid phase is slowly made basic with sodium bicarbonate (16.8 g., 0.2 mole), then with 40% aqueous sodium hydroxide (10 ml.) providing a heterogeneous mixture which is extracted with ether (100 ml.). The ethereal extract is washed with water and saturated aqueous brine, dried over sodium sulfate, and filtered. In vacuo evaporation of the filtrate leaves the title compound as a pale yellow, viscous oil.

EXAMPLE 27

Capsule Formulation

7-[3-(3-hydroxyoctyl)-4-oxo-2-thiazolidinyl]heptanoic acid — 50 g.

Stearic acid (U.S.P. triple pressure) — 125 g.
Pluronic F-68 — 7.5 g.
Corn Starch — 125 g.

The stearic acid and pluronic are united in a vessel and melted using a water bath at 60° to 65° C. The heating is discontinued and the 7-[3-(3-hydroxyoctyl)-4-oxo2-thiazolidinyl]heptanoic acid is dispersed into the mixture and the corn starch is added with stirring which is continued until the mixture cools to ambient temperature. The mixture is reduced to granules by screening and placed in a number 0 hard gelatin containing 307.5 mg. of total solids and 50 mg. of 7-[3-(3-hydroxyoctyl)-4-oxo-2-thiazolidinyl]heptanoic acid per capsule.

EXAMPLE 28

Parenteral Formulation of a Multidose Solution for Intramuscular and Intravenous Use 7-[3-(3-Hydroxyoctyl)-4-oxo-2-thiazolidinyl]-
  heptanoic acid 13 1 g.
Tris-(hydroxymethyl)aminomethane (Reagent Grade THAM) — q.s. to adjust solution to pH 7.4
Sodium Chloride (U.S.P.) — q.s. to yield isotonic solution
Methylparaben — 10 mg.
Polyparaben — 1 mg.
Distilled water (pyrogen-free) — q.s. to 10 ml.

The 7[3 -(3-hydroxyoctyl)-4-oxo-2-thiazolidinyl]-heptanoic acid suspended in about 6 ml. of the water is treated with tris-(hydroxymethyl)aminomethane with stirring until the pH reaches 7.4. The methylparaben and polyparaben are added with stirring and sufficient sodium chloride is added to produce an isotonic solution. After water is added to bring the final volume to 10 ml., the solution is sterilized by membrane filtration and placed in a vial by an aseptic technique. The solution contains the THAM salt of 7-[3-(3-hydroxyoctyl)-4-oxo-3-thiazolidinyl]heptanoic acid equivalent to 100 mg./ml. of the free acid.

EXAMPLE 29

Preparation of Suppositories

7-[3-(3-hydroxyoctyl)-4-oxo-2-thiazolidinyl]
  heptanoic acid — 200 g.
Butylated hydroxyanisole — 82 mg.
Butylated hydroxytoluene — 82 mg.
Ethylenediamine tetraacetic acid — 163 mg.
Glycerine, U.S.P. — 128 g.
Sodium chloride, microfine — 52.5 g.
Polyethylene glycol 6000 — 128 g.
Polyethylene glycol 4000 — 1269 g.

The polyethylene glycol 4000 and polyethylene glycol 6000 are placed in a vessel surrounded by a water bath at such a temperature as required to maintain the melted contents of 60° to 65° C. To the melt is added the butylated hydroxyanisole and butylated hydroxytoluene with stirring. Then the ethylenediamine tetraacetic acid and microfine sodium chloride are added to and dispersed in the mixture. The 7-[3-(3-hydroxyoctyl)-4-oxo-2-thiazolidinyl]heptanoic acid is then added and dispersed into the mixture. Finally, the temperature is lowered to 55° to 60° C. and the glycerine is added and dispersed.

While maintaining the temperature of 55° to 60° C. and continuous mixing, the melt is dispersed into plastic suppository cavities of a conventional suppository coldmolding device. The suppositories thus prepared contain a total of 1.7778 g of contents of which 200 mg. are 7-[3-(3-hydroxyoctyl)-4-oxo-2-thiazolidinyl]-heptanoic acid.

What is claimed is:
1. The compound of the formula

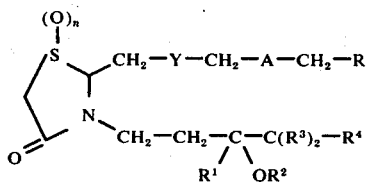

wherein
R is carboxy, a carboxy salt, or derivatized carboxy;
A is selected from the group consisting of methylene and oxygen;
Y is selected from the group consisting of ethylene, vinylene, and ethynylene;
n is 0, 1, or 2;
$R^1$ is hydrogen or methyl;
$R^2$ is hydrogen or lower alkanoyl of from 1–5 carbon atoms;
$R^3$ is hydrogen or methyl; and
$R^4$ is alkyl, branched chain alkyl of from 3–6 carbon atoms, 4,4,4-trifluorobutyl, or $OR^{4a}$ wherein $R^{4a}$ is alkyl, branched alkyl of from 2–5 carbon atoms, substituted alkyl including 3,3,3-trifluoropropyl, 5- or 6-membered heterocyclic ring containing nitrogen or oxygen, including pyridyl, or furfuryl, or phenyl in which the phenyl ring can be substituted with one or two substituents selected from the group consisting of halogen, methyl, methoxy, or trifluoromethyl; in addition, when $R^4$ is lower straight chain alkyl and $R^1$ is methyl, the terminal carbon atom of $R^4$ can be joined to $R^1$ to form a carbocyclic ring of from 6–9 carbon atoms, or when $R^4$ is straight chain alkyl and $R^1$ is hydrogen, the terminal carbon atom of $R^4$ can be joined to the carbon atom bearing $OR^2$ to form a carbocyclic ring of from 5–8 carbon atoms;
also, when $R^1$, $R^2$, and $R^3$ are hydrogen, $R^4$ can be a straight chain alkyl such that the terminal carbon atom of $R^4$ can be joined to the hydroxyl group oxygen atom to form a cyclic ether containing 5- or 6-membered atoms.

2. The compound of claim 1 wherein R is carboxy, a carboxy salt having the formula $-COO^-M^+$ in which M is a pharmaceutically-acceptable cation derived from a metal or an amine; or derivatized carboxy in which R is selected from alkoxycarbonyl ($-COOR^5$ wherein $R^5$ is alkyl having 1–10 carbon atoms); carbamoyl ($-CO_2NH_2$); substituted carbamoyl ($-CONR^6R^7$) wherein $R^6$ and $R^7$ are selected from the group consisting of hydrogen, lower alkyl having 1–4 carbon atoms, and diloweralkylaminoalkyl having 4–7 carbon atoms; and carbazoyl ($-CONHNH_2$).

3. Th compound of claim 2 wherein n is 0.
4. The compound of claim 3 wherein
A is methylene,
Y is ethylene,
$R^1$, $R^2$, and $R^3$ are hydrogen, and
R is carboxy.

5. The compound of claim 4 wherein $R^4$ is butyl, which is 7-[3-(3-hydroxyoctyl)-4-oxo-2-thiazolidinyl]-heptanoic acid.

6. The compound of claim 5 wherein the carbon bearing the $R^1$ and $OR^2$ substituents is in the "S" configuration, which is 7-[3-(3(S)-hydroxyoctyl)-4-oxo-2-thiazolidinyl]heptanoic acid.

7. The compound of claim 5 wherein the carbon bearing the $R^1$ and $OR^2$ substituents is in the "R" configuration, which is 7-[3-(3(R)-hydroxyoctyl)-4-oxo-2-thiazolidinyl]heptanoic acid.

8. The compound of claim 4 wherein $R^4$ is 4,4,4-trifluorobutyl, which is 7-[3-(3-hydroxy-8,8,8-trifluorooctyl)-4-oxo-2-thiazolidinyl]heptanoic acid.

9. The compound of claim 2 wherein
A is methylene,
Y is ethylene, and
$R^1$ and $R^3$ are hydrogen.

10. The compound of claim 9 wherein R is carboxy, $R^2$ is acetyl, and $R^4$ is butyl, which is 7-[3-(3-Acetyloxyoctyl)-4-oxo-2-thiazolidinyl]heptanoic acid.

11. The compound of claim 9 wherein R is N-(2-dimethylaminoethyl)carbamoyl, $R^2$ is hydrogen, and $R^4$ is butyl, which is N-(2-dimethylaminoethyl)-7-[3-(3-hydroxyoctyl)-4oxo-2-thiazolidinyl]heptanamide.

12. The compound of claim 4 wherein $R^4$ is propyl and the carbon atom of the propyl group is joined to the hydroxyl group oxygen with abstraction of hydrogen to form a 6-membered cyclic ether, which is 7-{3-[2-(tetrahydro-2H-pyran-2-yl)ethyl]-4-oxo-2-thiazolidinyl}heptanoic acid.

13. The compound of claim 4 wherein $R^4$ is butyl and the terminal carbon atom of the butyl group is joined to the carbon atom bearing the hydroxyl group with abstraction of hydrogen to form a 6-membered carbocyclic ring, which is 7-{3-[2-(1-hydroxycyclohexyl)ethyl]-4-oxo-2-thiazolidinyl}-heptanoic acid.

14. The compound of claim 14 wherein $R^4$ is propoxy, which is 7-[3-(3-hydroxy-4-propoxybutyl)-4-oxo-2-thiazolidinyl]heptanoic acid.

15. The compound of claim 3 wherein A is methylene, Y is ethylene, $R^1$ and $R^2$ are hydrogen, $R^3$ is methyl, and $R^4$ is butyl, which is 7-[3-(3-hydroxy-4,4-dimethyloctyl)-4-oxo-2-thiazolidinyl]heptanoic acid.

16. The compound of claim 3 wherein A is methylene, Y is ethylene, $R^1$ is methyl, $R^2$ and $R^3$ are hydrogen, and $R^4$ is butyl, which is 7-[3-(3-hydroxy-3-methyloctyl)-4-oxo-2-thiazolidinyl]heptanoic acid.

17. The compound of claim 4 wherein $R^4$ is 3-pyridyloxy, which is 7-{3-[3-hydroxy-4-(3-pyridyloxy)butyl]4-oxo-2-thiazolidinyl}heptanoic acid.

18. The compound of claim 4 wherein $R^4$ is 4fluorophenoxy, which is 7-{3-[3-hydroxy-4-(4-fluorophenoxy)butyl]-4-oxo-2-thiazolidinyl heptanoic acid.

19. The compound of claim 3 wherein
A is oxygen,
$R^1$, $R^2$, and $R^3$ are hydrogen, and
$R^4$ is butyl.

20. The compound of claim 19 wherein Y is ethynylene, which is 3-oxa-7-[3-(3-hydroxyoctyl)-4-oxo-2-thiazolidinyl]-5-heptynoic acid.

21. The compound of claim 19 wherein Y is cisvinylene, which is 3-oxa-7-[3-(3-hydroxyoctyl)-4-oxo-2-thiazolidinyl]-5-cis-heptenoic acid.

22. The compound of claim 19 wherein Y is ethylene, which is 3-oxa-7-[3-(3-hydroxyoctyl)-4-oxo-2-thiazolidinyl]heptanoic acid.

23. The compound of claim 2 wherein n is 1.
24. The compound of claim 23 wherein
A is methylene,
Y is ethylene, and
$R^1$, $R^2$, and $R^3$ are hydrogen.

25. The compound of claim 24 wherein R is carboxy.
26. The compound of claim 25 wherein $R^4$ is butyl, which is 7-[3-(3-hydroxyoctyl)-1,4-dioxo-2-thiazolidinyl]heptanoic acid.

27. The compound of claim 25 wherein $R^4$ is propoxy, which is 7-[3-(3-hydroxy-4-propoxybutyl)-1,4-dioxo-2-thiazolidinyl]heptanoic acid.

28. The compound of claim 24 wherein R is ethoxycarbonyl and $R^4$ is propoxy, which is ethyl 7-[3-(3-hydroxy4-propoxybutyl)-1,4-dioxo-2-thiazolidinyl]-heptanoate.

29. The compound of claim 23 wherein
R is carboxy,
A is oxygen,
$R^1$, $R^2$, and $R^3$ are hydrogen, and
$R^4$ is butyl.

30. The compound of claim 29 wherein Y is cisvinylene, which is 3-oxa-73-(3-hydroxyoctyl)-1,4-dioxo-2-thiazolidinyl]-5-cis-heptenoic acid.

31. The compound of claim 29 wherein Y is ethylene, which is 3-oxa-7-[3-(3-hydroxyoctyl)-1,4-dioxo-2-thiazolidinyl]heptanoic acid.

32. The compound of claim 2 wherein n is 2.
33. The compound of claim 32 wherein
R is carboxy,
A is methylene,
Y is ethylene, and
$R^1$, $R^2$, and $R^3$ are hydrogen.

34. The compound of claim 33 wherein $R^4$ is butyl, which is 7-[3-(3-hydroxyoctyl)-1,1,4-trioxo-2-thiazolidinyl]-heptanoic acid.

35. The compound of claim 32 wherein
R is carboxy,
A is oxygen,
$R^1$, $R^2$, and $R^3$ are hydrogen, and
$R^4$ is butyl.

36. The compound of claim 35 wherein y is cisvinylene, which is 3-oxa-7-[3-(3-hydroxyoctyl)-1,1,4-trioxo-2-thiazolidinyl]-5-cis-heptenoic acid.

37. The compound of claim 32 wherein
R is carboxy,
A is methylene,
Y is ethylene, and
$R^1$, $R^2$, and $R^3$ are hydrogen.

38. The compound of claim 37 wherein $R^4$ is propoxy, which is 7-[3-(3-hydroxy-4-propoxybutyl)-1,1,4trioxo-2-thiazolidinyl]-heptanoic acid.

39. A process for the preparation of compounds of the formula $$\underset{O}{\overset{(O)_n}{\underset{\|}{S}}}\diagdown\underset{N}{\overset{}{\bigvee}}\diagup\overset{CH_2-Y-CH_2-A-CH_2-CO_2H}{\underset{CH_2-CH_2-\underset{R^1}{\overset{}{C}}-C(R^3)_2-R^4}{|}}$$

wherein
A is selected from the group consisting of methylene and oxygen;
Y is selected from the group consisting of ethynylene, cis-vinylene, and ethylene;
n is 0, 1 or 2;
$R^1$ is methyl or hydrogen;

$R^3$ is independently selected from the group consisting of hydrogen and methyl; and $R^4$ is selected from the group consisting of alkyl or branched alkyl of 3–6 carbon atoms (e.g., propyl, butyl, hexyl, isoamyl, 3,3-dimethylbutyl), or 4,4,4-trifluorobutyl; in addition, when $R^4$ is straight chain alkyl and $R^1$ is methyl, the terminal carbon atom of $R^4$ can be joined to $R^1$ (with abstraction of hydrogen) to form a carbocyclic ring of from 6–9 carbon atoms, or when $R^4$ is straight chain alkyl and $R^1$ is hydrogen, the terminal carbon atom of $R^4$ can be joined to the carbon bearing the hydroxyl group to form a carbocyclic ring of from 5–8 carbon atoms; also, when $R^1$, $R^2$, and $R^3$ are hydrogen, $R^4$ can be straight chain alkyl such that the terminal carbon atom of $R^4$ is joined to the hydroxy group oxygen atom (with abstraction of hydrogen) to form a cyclic ether containing 5- or 6-membered forms; and, further, $R^4$ can be $OR^{4a}$ where $R^{4a}$ is alkyl, branched alkyl of from 2–5 carbon atoms, substituted alkyl including 3,3,3-trifluoropropyl, 5- or 6-membered heterocyclic ring containing nitrogen or oxygen including pyridyl, furfuryl, furyl, or phenyl in which the phenyl ring can be substituted with one or two substituents selected from the group consisting of halogen, methyl, methoxy, or trifluoromethyl;

which comprises condensation of an aldehyde of the formula

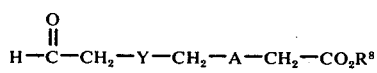

wherein A and y are as previously defined and $R^8$ is straight chain lower alkyl (methyl or ethyl), with an amine of the formula

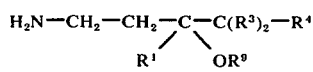

wherein $R^1$, $R^3$, and $R^4$ are as defined above and $R^9$ is the tetrahydro-2H-pyran-2-yl moiety, in the presence of a suitable inorganic drying agent such as sodium or magnesium sulfate to produce an imine of the formula

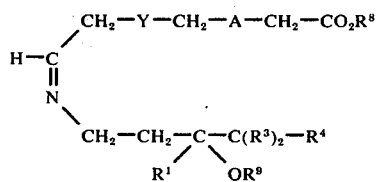

wherein A, Y, $R^1$, $R^3$, $R^4$, $R^8$, and $R^9$ are as previously defined, condensing said imine with mercaptoacetic acid to effect initial thiol addition to the imine and subsequent ring closure of the intermediate amine acid with resultant production of a substituted 4-oxothiazolidine of the formula

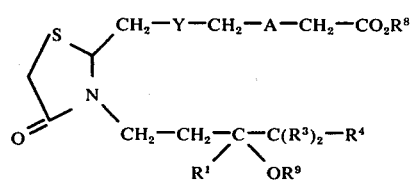

wherein A, y, $R^1$, $R^3$, $R^4$, $R^8$ and $R^9$ are as previously defined, hydrolyzing the $R^9$ and $R^8$ protecting groups of said substituted 4-oxothiazolidine in acidic protic media and dilute aqueous alkalai, respectively, to provide an acid of the formula

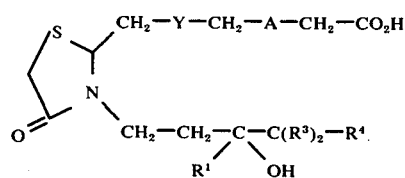

wherein A, Y, $R^1$, $R^3$, and $R^4$ are as previously defined, and oxidizing said acid to form a substituted 1,4-dioxothiazolidine or 1,1,4-trioxothiazolidine of the formula

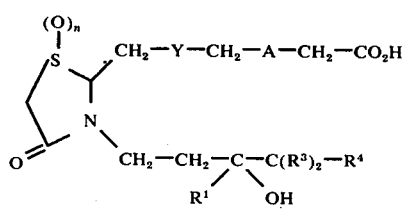

wherein A, Y, n, $R^1$, $R^3$, and $R^4$ are as previously defined.

* * * * *